United States Patent
Almogy et al.

(10) Patent No.: US 11,584,963 B2
(45) Date of Patent: Feb. 21, 2023

(54) METHODS FOR SEQUENCING WITH SINGLE FREQUENCY DETECTION

(71) Applicant: ULTIMA GENOMICS, INC., Newark, CA (US)

(72) Inventors: Gilad Almogy, Palo Alto, CA (US); Florian Oberstrass, Menlo Park, CA (US)

(73) Assignee: ULTIMA GENOMICS, INC., Newark, CA (US)

( * ) Notice: Subject to any disclaimer, the term of this patent is extended or adjusted under 35 U.S.C. 154(b) by 180 days.

(21) Appl. No.: 16/945,173

(22) Filed: Jul. 31, 2020

(65) Prior Publication Data

US 2021/0017593 A1     Jan. 21, 2021

Related U.S. Application Data

(63) Continuation of application No. PCT/US2019/018287, filed on Feb. 15, 2019.

(60) Provisional application No. 62/710,483, filed on Feb. 16, 2018.

(51) Int. Cl.
*C12Q 1/6869*     (2018.01)
*C12Q 1/6876*     (2018.01)

(52) U.S. Cl.
CPC ......... *C12Q 1/6869* (2013.01); *C12Q 1/6876* (2013.01)

(58) Field of Classification Search
None
See application file for complete search history.

(56) References Cited

U.S. PATENT DOCUMENTS

| | | | |
|---|---|---|---|
| 7,476,503 B2 | 1/2009 | Turner et al. | |
| 8,252,911 B2 | 8/2012 | Bjornson et al. | |
| 8,632,975 B2 | 1/2014 | Vander Horn et al. | |
| 8,652,781 B2 | 2/2014 | Korlach | |
| 9,222,132 B2 | 12/2015 | Drmanac | |
| 9,932,631 B1 | 4/2018 | Dambacher et al. | |
| 9,951,385 B1 | 4/2018 | Vijayan et al. | |
| 2013/0079232 A1 | 3/2013 | Kain et al. | |
| 2017/0137873 A1 | 5/2017 | Nguyen et al. | |
| 2017/0343479 A1 | 11/2017 | Turner et al. | |
| 2017/0369857 A1 | 12/2017 | Vander Horn et al. | |
| 2018/0044727 A1 | 2/2018 | Vijayan et al. | |
| 2018/0208983 A1 | 7/2018 | Dambacher et al. | |

FOREIGN PATENT DOCUMENTS

| | | | |
|---|---|---|---|
| WO | WO-2017117235 A1 | 7/2017 | |
| WO | WO-2017184996 A1 | 10/2017 | |
| WO | WO-2019161253 A1 | 8/2019 | |

OTHER PUBLICATIONS

Chen, et al. The history and advances of reversible terminators used in new generations of sequencing technology. Genomics, Proteomics & Bioinformatics 11.1 (2013): 34-40.
Dahl, et al. Modulation of DNA polymerase noncovalent kinetic transitions by divalent cations. Journal of Biological Chemistry 291.12 (2016): 6456-6470.
PCT/US19/18287 International Search Report dated May 14, 2019.
Tabor, et al., Effect of manganese ions on the incorporation of dideoxynucleotides by bacteriophage T7 DNA polymerase and Escherichia coli DNA polymerase I, Proc. Natl. Acad. Sci. USA, Jun. 1989, 86:4076-80.

*Primary Examiner* — Teresa E Strzelecka
(74) *Attorney, Agent, or Firm* — Wilson Sonsini Goodrich & Rosati

(57) ABSTRACT

The present disclosure provides methods and systems for sequencing nucleic acid molecules using a single frequency during detection, or fewer frequencies than types of nucleotide bases identified during detection. Methods and systems of the present disclosure may involve transiently binding nucleotides. Methods and systems provided herein may enable sequences to be determined at a higher accuracy and efficiency.

18 Claims, 3 Drawing Sheets

METHODS FOR SEQUENCING WITH SINGLE FREQUENCY DETECTION

CROSS-REFERENCE

This is a continuation of International Application No. PCT/US2019/018287, filed Feb. 15, 2019, which claims the benefit of U.S. Provisional Patent Application No. 62/710,483, filed Feb. 16, 2018, each of which applications is entirely incorporated herein by reference.

BACKGROUND

The detection, quantification and sequencing of nucleic acid molecules (e.g., polynucleotides) may be important for molecular biology and medical applications, such as diagnostics. Genetic testing may be useful for a number of diagnostic methods. For example, disorders that are caused by rare genetic alterations (e.g., sequence variants) or changes in epigenetic markers, such as cancer and partial or complete aneuploidy, may be detected or more accurately characterized with deoxyribonucleic acid (DNA) or ribonucleic acid (RNA) sequence information.

Elucidating the entire human genome has created interest in technologies for rapid nucleic acid (e.g., DNA) sequencing, both for small- and large-scale applications. Some important parameters are sequencing speed, sequencing accuracy, length of sequence that can be read during a single sequencing run, and amount of nucleic acid template required to generate sequencing information. Large scale genome projects may be too expensive to be practicable for analyzing a large number of subjects (e.g., patients). Furthermore, as knowledge of the genetic bases for human diseases increases, the need for accurate, high-throughput DNA sequencing that is affordable will also increase. Practical methods for determining the base pair sequences of single molecules of nucleic acids, preferably with high speed, high accuracy and long read lengths, may provide measurement capability.

Nucleic acid sequencing is a process that can be used to provide sequence information for a nucleic acid sample. Such sequence information may be helpful in diagnosing and/or treating a subject with a condition. For example, the nucleic acid sequence of a subject may be used to identify, diagnose and potentially develop treatments for genetic diseases. As another example, research into pathogens may lead to treatment of contagious diseases.

SUMMARY

Sequencing reads may contain errors from various sources. For example, the accuracy of sequencing reads may be lower at certain genomic loci than at other loci, such as where there are homopolymer repeats or other repeats (e.g., dinucleotide repeats, trinucleotide repeats, etc.) in the sequence. Sequencing reads may contain errors where unlabeled or otherwise undetectable nucleotides are incorporated into a nucleic acid template (or clone thereof). A sequencing instrument may not be able to detect or resolve signals, such as optical signals from fluorescently-labeled nucleotides. Such limitations can render sequencing inaccurate, inefficient, or ineffective for use in various applications, such as biological applications aiming to accurately identify various genetic variants. Recognized herein is the need for methods and systems to address at least the abovementioned limitations.

Methods and systems of the present disclosure may detect optical signals from transiently bound nucleotides to determine sequencing reads at higher accuracy and efficiency.

In an aspect, provided is a method for nucleic acid sequencing, comprising: (a) providing a substrate comprising at least a first set of nucleic acid molecules and a second set of nucleic acid molecules, wherein nucleic acid molecules of the first set have sequence homology to a first template and nucleic acid molecules of the second set have sequence homology to a second template, wherein the first template is different than the second template; (b) bringing the first set of nucleic acid molecules and the second set of nucleic acid molecules in contact with a reaction mixture comprising nucleotides of at least two different types, under conditions sufficient to permit transient binding of at least a subset of the nucleotides to nucleic acid molecules of the first set of nucleic acid molecules and the second set of nucleic acid molecules; (c) detecting a first optical signal from the first set of nucleic acid molecules and a second signal from the second set of nucleic acid molecules, wherein the first optical signal and the second optical signal have the same frequency, and wherein the first optical signal and the second optical signal have different intensities; and (d) using intensities of the first optical signal and the second optical signal to identify types of nucleotides transiently bound to the nucleic acid molecules of the first set of nucleic acid molecules and the nucleic acid molecules of the second set of nucleic acid molecules, thereby sequencing the nucleic acid molecules of the first set and the second set of nucleic acid molecules.

In some embodiments, the nucleotides are configured to permit transient binding.

In some embodiments, the conditions sufficient to permit transient binding include presence of a metal cation. In some embodiments, the metal cation is selected from a group consisting of calcium, scandium, titanium, vanadium, chromium, iron, cobalt, nickel, copper, zinc, gallium, germanium, arsenic, selenium, rhodium, and strontium.

In some embodiments, the method further comprises, subsequent to (d), removing the nucleotides transiently bound to the nucleic acid molecules of the first set of nucleic acid molecules and the nucleic acid molecules of the second set of nucleic acid molecules.

In some embodiments, the method further comprises heating the substrate to remove the nucleotides transiently bound to the nucleic acid molecules of the first set of nucleic acid molecules and the nucleic acid molecules of the second set of nucleic acid molecules.

In some embodiments, the method further comprises bringing the first set of nucleic acid molecules and the second set of nucleic acid molecules in contact with an additional reaction mixture comprising nucleotides of at least two types, under conditions sufficient to permit non-transient binding of at least a subset of the nucleotides from the additional reaction mixture to the nucleic acid molecules of the first set of nucleic acid molecules and the second set of nucleic acid molecules.

In some embodiments, the method further comprises repeating (b)-(d) with another reaction mixture comprising nucleotides of at least two different types, under conditions sufficient to permit transient binding of at least a subset of the nucleotides to the nucleic acid molecules of the first set of nucleic acid molecules and the second set of nucleic acid molecules.

In some embodiments, the reaction mixture comprises a first set of nucleotides of a first type and a second set of nucleotides of a second type, wherein the first set and the second set of nucleotides include labeled nucleotides, and wherein the first set or the second set of nucleotides includes unlabeled nucleotides.

In some embodiments, the first set and the second set of nucleotides include unlabeled nucleotides.

In some embodiments, the first set of nucleotides has a first ratio of labeled to unlabeled nucleotides and the second set of nucleotides has a second ratio of labeled to unlabeled nucleotides, which first ratio is different than the second ratio. In some embodiments, the first set of nucleotides includes analogs of guanine, and wherein the first ratio is less than the second ratio.

In some embodiments, the labeled nucleotides of the first type and the labeled nucleotides of the second type are labeled by the same dye and excited by the same frequency.

In some embodiments, the labeled nucleotides of the first type and the labeled nucleotides of the second type are labeled by different dyes and excited by the same frequency.

In some embodiments, the reaction mixture comprises nucleotides of at least three different types.

In some embodiments, the reaction mixture comprises nucleotides of four different types.

In another aspect, provided is a method for nucleic acid sequencing, comprising: (a) providing a substrate comprising at least a first set of nucleic acid molecules and a second set of nucleic acid molecules, wherein nucleic acid molecules of the first set have sequence homology to a first template and nucleic acid molecules of the second set have sequence homology to a second template, wherein the first template is different than the second template; (b) bringing the first set of nucleic acid molecules and the second set of nucleic acid molecules in contact with a reaction mixture comprising at least four different types of labeled nucleotides, under conditions sufficient to permit transient binding of at least a subset of the at least four different types of labeled nucleotides to nucleic acid molecules of the first set of nucleic acid molecules and the second set of nucleic acid molecules; (c) detecting a first optical signal from the first set of nucleic acid molecules and a second signal from the second set of nucleic acid molecules, wherein the first optical signal and the second optical signal have the same frequency, and wherein the first optical signal and the second optical signal have different intensities; and (d) using intensities of the first optical signal and the second optical signal to identify types of nucleotides transiently bound to the nucleic acid molecules of the first set of nucleic acid molecules and the nucleic acid molecules of the second set of nucleic acid molecules, thereby sequencing the nucleic acid molecules of the first set and the second set of nucleic acid molecules.

In some embodiments, the labeled nucleotides are configured to permit transient binding.

In some embodiments, the conditions sufficient to permit transient binding include presence of a metal cation. In some embodiments, the metal cation is selected from a group consisting of calcium, scandium, titanium, vanadium, chromium, iron, cobalt, nickel, copper, zinc, gallium, germanium, arsenic, selenium, rhodium, and strontium.

In some embodiments, the method further comprises, subsequent to (d), removing the labeled nucleotides transiently bound to the nucleic acid molecules of the first set of nucleic acid molecules and the nucleic acid molecules of the second set of nucleic acid molecules. In some embodiments, the method further comprises heating the substrate to remove the labeled nucleotides transiently bound to the nucleic acid molecules of the first set of nucleic acid molecules and the nucleic acid molecules of the second set of nucleic acid molecules. In some embodiments, the method further comprises bringing the first set of nucleic acid molecules and the second set of nucleic acid molecules in contact with an additional reaction mixture comprising nucleotides of at least two types, under conditions sufficient to permit non-transient binding of at least a subset of the nucleotides from the additional reaction mixture to the nucleic acid molecules of the first set of nucleic acid molecules and the second set of nucleic acid molecules. In some embodiments, the method further comprises repeating (b)-(d) with another reaction mixture comprising nucleotides of at least two different types, under conditions sufficient to permit transient binding of at least a subset of the nucleotides to the nucleic acid molecules of the first set of nucleic acid molecules and the second set of nucleic acid molecules.

In some embodiments, the reaction mixture comprises a first set of unlabeled nucleotides of a first type and a second set of unlabeled nucleotides of a second type. In some embodiments, the reaction mixture comprises at least three different types of unlabeled nucleotides. In some embodiments, the reaction mixture comprises at least four different types of unlabeled nucleotides. In some embodiments, a first set of nucleotides of a first type in the reaction mixture has a first ratio of labeled to unlabeled nucleotides and a second set of nucleotides of a second type in the reaction mixture has a second ratio of labeled to unlabeled nucleotides, which first ratio is different than the second ratio, wherein the first type is different than the second type. In some embodiments, the first set of nucleotides includes analogs of guanine, and wherein the first ratio is less than the second ratio. In some embodiments, the labeled nucleotides of the first type and the labeled nucleotides of the second type are labeled by the same dye and excited by the same frequency. In some embodiments, the labeled nucleotides of the first type and the labeled nucleotides of the second type are labeled by different dyes and excited by the same frequency.

In some embodiments, the substrate comprises a third set of nucleic acid molecules and a fourth set of nucleic acid molecules, wherein nucleic acid molecules of the third set have sequence homology to a third template different than the first template and the second template, and wherein nucleic acid molecules of the fourth set have sequence homology to a fourth template different than the first template, the second template, and the third template, wherein (c) comprises detecting a third optical signal from the third set of nucleic acid molecules and a fourth optical signal from the fourth set of nucleic acid molecules, wherein the third optical signal and the fourth optical signal have the same frequency, and wherein the third optical signal and the fourth optical signal have different intensities.

In some embodiments, the third optical signal and the fourth optical signal have the same frequency as the first optical signal and the second optical signal.

In some embodiments, (d) comprises using intensities of the first optical signal, the second optical signal, the third optical signal, and the fourth optical signal, respectively, to identify types of nucleotides transiently bound to the nucleic acid molecules of the third set of nucleic acid molecules and the nucleic acid molecules of the fourth set of nucleic acid molecules, thereby sequencing the nucleic acid molecules of the third set and the fourth set of nucleic acid molecules.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1:
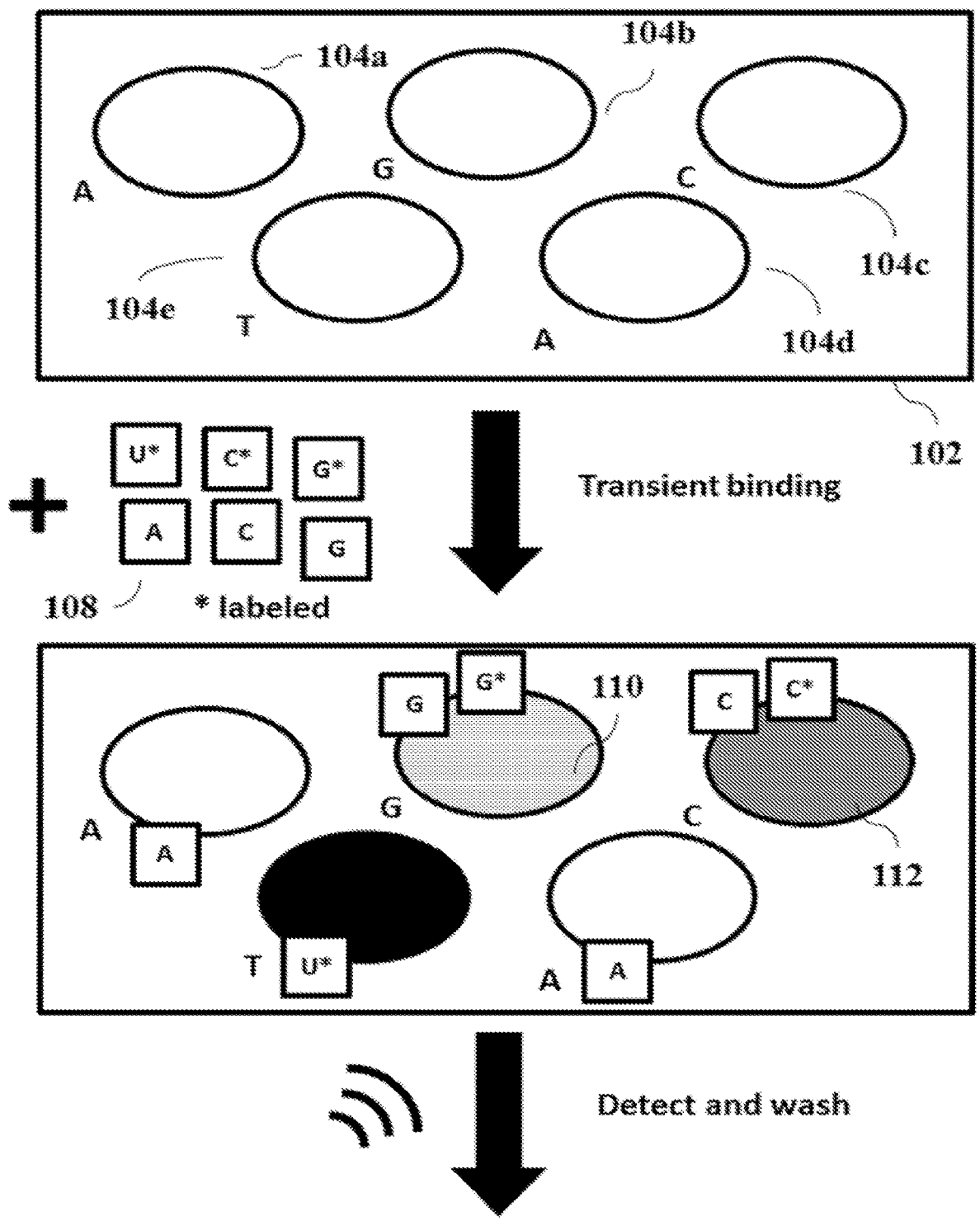
FIG. 1 illustrates a method for sequencing to identify four different base types using a single frequency.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "sequencing," as used herein, generally refers to a process for generating or identifying a sequence of a biological molecule, such as a nucleic acid molecule or a polypeptide. Such sequence may be a nucleic acid sequence, which may include a sequence of nucleic acid bases. Sequencing may be single molecule sequencing or sequencing by synthesis, for example. Sequencing may be performed using template nucleic acid molecules immobilized on a support, such as a flow cell or one or more beads.

The term "biological sample," as used herein, generally refers to any sample from a subject. The biological sample can be a fluid or tissue from the subject. The fluid can be blood (e.g., whole blood), saliva, urine, or sweat. The tissue can be from an organ (e.g., liver, lung, or thyroid), or a mass of cellular material, such as, for example, a tumor. The biological sample can be a feces sample, collection of cells (e.g., cheek swab), or hair sample. The biological sample can be a cell-free or cellular sample. Examples of biological samples include nucleic acid molecules, amino acids, polypeptides, proteins, carbohydrates, fats, or viruses. In an example, a biological sample is a nucleic acid sample including one or more nucleic acid molecules, such as deoxyribonucleic acid (DNA) and/or ribonucleic acid (RNA). The nucleic acid molecules may be cell-free or cell-free nucleic acid molecules, such as cell free DNA or cell free RNA. The nucleic acid molecules may be derived from a variety of sources including human, mammal, non-human mammal, ape, monkey, chimpanzee, reptilian, amphibian, or avian, sources. Further, samples may be extracted from variety of animal fluids containing cell free sequences, including but not limited to blood, serum, plasma, vitreous, sputum, urine, tears, perspiration, saliva, semen, mucosal excretions, mucus, spinal fluid, amniotic fluid, lymph fluid and the like. Cell free polynucleotides may be fetal in origin (via fluid taken from a pregnant subject), or may be derived from tissue of the subject itself.

The term "subject," as used herein, generally refers to an individual from whom a biological sample is obtained. The subject may be a mammal or non-mammal. The subject may be an animal, such as a human, monkey, dog, cat, bird, or rodent. The subject may be a patient. The subject may be displaying a disease or a symptom of a disease. The subject may be asymptomatic. The subject may be undergoing treatment. The subject may not be undergoing treatment. The subject can have or be suspected of having a disease, such as cancer (e.g., breast cancer, colorectal cancer, brain cancer, leukemia, lung cancer, skin cancer, liver cancer, pancreatic cancer, lymphoma, esophageal cancer or cervical cancer) or an infectious disease. The subject can have or be suspected of having a genetic disorder such as achondroplasia, alpha-1 antitrypsin deficiency, antiphospholipid syndrome, autism, autosomal dominant polycystic kidney disease, Charcot-Marie-tooth, cri du chat, Crohn's disease, cystic fibrosis, Dercum disease, down syndrome, Duane syndrome, Duchenne muscular dystrophy, factor V Leiden thrombophilia, familial hypercholesterolemia, familial Mediterranean fever, fragile x syndrome, Gaucher disease, hemochromatosis, hemophilia, holoprosencephaly, Huntington's disease, Klinefelter syndrome, Marfan syndrome, myotonic dystrophy, neurofibromatosis, Noonan syndrome, osteogenesis imperfecta, Parkinson's disease, phenylketonuria, Poland anomaly, porphyria, progeria, retinitis pigmentosa, severe combined immunodeficiency, sickle cell disease, spinal muscular atrophy, Tay-Sachs, thalassemia, trimethylaminuria, Turner syndrome, velocardiofacial syndrome, WAGR syndrome, or Wilson disease.

The terms "nucleic acid," "nucleic acid molecule," "nucleic acid sequence," "nucleic acid fragment," "oligonucleotide" and "polynucleotide," as used herein, generally refer to a polynucleotide that may have various lengths, such as either deoxyribonucleotides or deoxyribonucleic acids (DNA) or ribonucleotides or ribonucleic acids (RNA), or analogs thereof. Non-limiting examples of nucleic acids include DNA, RNA, genomic DNA or synthetic DNA/RNA or coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant nucleic acids, branched nucleic acids, plasmids, vectors, isolated DNA of any sequence, and isolated RNA of any sequence. A nucleic acid molecule can have a length of at least about 10 nucleic acid bases ("bases"), 20 bases, 30 bases, 40 bases, 50 bases, 100 bases, 200 bases, 300 bases, 400 bases, 500 bases, 1 kilobase (kb), 2 kb, 3, kb, 4 kb, 5 kb, 10 kb, 50 kb, or more. An oligonucleotide can comprise a sequence of four natural nucleotide bases: adenine (A); cytosine (C); guanine (G); and thymine (T) (uracil (U) for thymine (T) when the polynucleotide is RNA). Oligonucleotides may include one or more nonstandard nucleotide(s), nucleotide analog(s) and/or modified nucleotide(s).

Nonstandard nucleotides, nucleotide analogs, and/or modified analogs may include, but are not limited to, diaminopurine, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D- mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5- oxyacetic acid methylester, uracil-5-oxyacetic acid(v), 5-methyl-2-thiouracil, 3-(3-amino-3-N-2-carboxypropyl) uracil, (acp3)w, 2,6-diaminopurine, ethynyl nucleotide bases, 1-propynyl nucleotide bases, azido nucleotide bases, phosphoroselenoate nucleic acids and the like. In some cases, nucleotides may include modifications in their phosphate moieties, including modifications to a triphosphate moiety. Additional, non-limiting examples of modifications include phosphate chains of greater length (e.g., a phosphate chain having, 4, 5, 6, 7, 8, 9, 10 or more phosphate moieties), modifications with thiol moieties (e.g., alpha-thio triphosphate and beta-thiotriphosphates) or modifications with selenium moieties (e.g., phosphoroselenoate nucleic acids). Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as aminoallyl-dUTP (aa-dUTP) and aminohexhylacrylamide-dCTP (aha-dCTP) to allow covalent attachment of amine reactive moieties, such as N-hydroxysuccinimide esters (NHS). Alternatives to standard DNA base pairs or RNA base pairs in the oligonucleotides of the present disclosure can provide higher density in bits per cubic mm, higher safety (resistant to accidental or purposeful synthesis of natural toxins), easier discrimination in photo-programmed polymerases, or lower secondary structure. Such alternative base pairs compatible with natural and mutant polymerases for de novo and/or amplification synthesis are described in Betz K, Malyshev D A, Lavergne T, Welte W, Diederichs K, Dwyer T J, Ordoukhanian P, Romesberg F E, Marx A. Nat. Chem. Biol. 2012 July; 8(7):612-4, which is herein incorporated by reference for all purposes. Nucleotide analogs may be capable of reacting or bonding with detectable moieties for nucleotide detection.

The term "reversible terminator," as used herein, generally refers to a moiety of a nucleotide analog that is capable of terminating primer extension reversibly. Nucleotide analogs comprising reversible terminators are accepted by polymerases and incorporated into growing nucleic acid sequences analogously to non-reversibly terminated nucleotides and nucleotide analogs. Following incorporation of a nucleotide analog comprising a reversible terminator into a nucleic acid strand, the reversible terminator may be removed to permit further extension of the nucleic acid strand. A reversible terminator may comprise a blocking or capping group that is attached to the 3'-oxygen atom of a sugar moiety (e.g., a pentose) of a nucleotide or nucleotide analog. Such moieties are referred to as 3'-O-blocked reversible terminators. Examples of 3'-O-blocked reversible terminators include, for example, 3'-ONH$_2$ reversible terminators, 3'-O-allyl reversible terminators, and 3'-O-aziomethyl reversible terminators. Alternatively, a reversible terminator may comprise a blocking group in a linker (e.g., a cleavable linker) and/or dye moiety of a nucleotide analog. Such moieties are referred to as 3'-unblocked reversible terminators. 3'-unblocked reversible terminators may be attached to both the base of the nucleotide analog as well as a fluorescing group (e.g., label, as described herein). Examples of 3'-unblocked reversible terminators include, for example, the "virtual terminator" developed by Helicos BioSciences Corp. and the "lightning terminator" developed by Michael L. Metzker and co-workers. Cleavage of a reversible terminator may be achieved by, for example, irradiating a nucleic acid molecule including the reversible terminator.

The term "homopolymer," as used herein, generally refers to a polymer or a portion of a polymer comprising identical monomer units. A homopolymer may have a homopolymer sequence. A nucleic acid homopolymer may refer to a polynucleotide or an oligonucleotide comprising consecutive repetitions of a same nucleotide or any nucleotide variants thereof. For example, a homopolymer can be poly (dA), poly(dT), poly(dG), poly(dC), poly(rA), poly(U), poly (rG), or poly(rC). A homopolymer can be of any length. For example, the homopolymer can have a length of at least 2, 3, 4, 5, 10, 20, 30, 40, 50, 100, 200, 300, 400, 500, or more nucleic acid bases. The homopolymer can have from 10 to 500, or 15 to 200, or 20 to 150 nucleic acid bases. The homopolymer can have a length of at most 500, 400, 300, 200, 100, 50, 40, 30, 20, 10, 5, 4, 3, or 2 nucleic acid bases. A molecule, such as a nucleic acid molecule, can include one or more homopolymer portions and one or more non-homopolymer portions. The molecule may be entirely formed of a homopolymer, multiple homopolymers, or a combination of homopolymers and non-homopolymers.

The terms "amplifying," "amplification," and "nucleic acid amplification" are used interchangeably and generally refer to generating one or more copies of a nucleic acid or a template. For example, "amplification" of DNA generally refers to generating one or more copies of a DNA molecule. Moreover, amplification of a nucleic acid may linear, exponential, or a combination thereof. Amplification may be emulsion based or may be non-emulsion based. Non-limiting examples of nucleic acid amplification methods include reverse transcription, primer extension, polymerase chain reaction (PCR), ligase chain reaction (LCR), helicase-dependent amplification, asymmetric amplification, rolling circle amplification, and multiple displacement amplification (MDA). Where PCR is used, any form of PCR may be used, with non-limiting examples that include real-time PCR, allele-specific PCR, assembly PCR, asymmetric PCR, digital PCR, emulsion PCR, dial-out PCR, helicase-dependent PCR, nested PCR, hot start PCR, inverse PCR, methylation-specific PCR, miniprimer PCR, multiplex PCR, nested PCR, overlap-extension PCR, thermal asymmetric interlaced PCR and touchdown PCR. Moreover, amplification can be conducted in a reaction mixture comprising various components (e.g., a primer(s), template, nucleotides, a polymerase, buffer components, co-factors, etc.) that participate or facilitate amplification. In some cases, the reaction mixture comprises a buffer that permits context independent incorporation of nucleotides. Non-limiting examples include magnesium-ion, manganese-ion and isocitrate buffers. Additional examples of such buffers are described in Tabor, S. et al. C. C. PNAS, 1989, 86, 4076-4080 and U.S. Pat. Nos. 5,409,811 and 5,674,716, each of which is herein incorporated by reference in its entirety.

Useful methods for clonal amplification from single molecules include rolling circle amplification (RCA) (Lizardi et al., Nat. Genet. 19:225-232 (1998), which is incorporated herein by reference), bridge PCR (Adams and Kron, Method for Performing Amplification of Nucleic Acid with Two Primers Bound to a Single Solid Support, Mosaic Technologies, Inc. (Winter Hill, Mass.); Whitehead Institute for Biomedical Research, Cambridge, Mass., (1997); Adessi et al., Nucl. Acids Res. 28:E87 (2000); Pemov et al., Nucl. Acids Res. 33:e11(2005); or U.S. Pat. No. 5,641,658, each of which is incorporated herein by reference), polony generation (Mitra et al., Proc. Natl. Acad. Sci. USA 100:5926-5931 (2003); Mitra et al., Anal. Biochem. 320:55-65(2003), each of which is incorporated herein by reference), and clonal amplification on beads using emulsions (Dressman et al., Proc. Natl. Acad. Sci. USA 100:8817-8822 (2003), which is incorporated herein by reference) or ligation to bead-based adapter libraries (Brenner et al., Nat. Biotechnol. 18:630-634 (2000); Brenner et al., Proc. Natl. Acad. Sci. USA 97:1665-1670 (2000)); Reinartz, et al., Brief Funct. Genomic Proteomic 1:95-104 (2002), each of which is incorporated herein by reference). The enhanced signal-to-noise ratio provided by clonal amplification more than outweighs the disadvantages of the cyclic sequencing requirement.

The term "polymerase," as used herein, generally refers to any enzyme capable of catalyzing a polymerization reaction. The polymerase used herein can have strand displacement activity or non-strand displacement activity. Examples of polymerases include, without limitation, a nucleic acid polymerase. The polymerase can be naturally occurring or synthesized. In some cases, a polymerase has relatively high processivity. An example polymerase is a Φ29 DNA polymerase or a derivative thereof. A polymerase can be a polymerization enzyme. In some cases, a transcriptase or a ligase is used (i.e., enzymes which catalyze the formation of a bond). Examples of polymerases include a DNA polymerase, an RNA polymerase, a thermostable polymerase, a wild-type polymerase, a modified polymerase, E. coli DNA polymerase I, T7 DNA polymerase, bacteriophage T4 DNA polymerase Φ29 (phi29) DNA polymerase, Taq polymerase, Tth polymerase, Tli polymerase, Pfu polymerase, Pwo polymerase, VENT polymerase, DEEPVENT polymerase, EX-Taq polymerase, LA-Taq polymerase, Sso polymerase, Poc polymerase, Pab polymerase, Mth polymerase, ES4 polymerase, Tru polymerase, Tac polymerase, Tne polymerase, Tma polymerase, Tea polymerase, Tih polymerase, Tfi polymerase, Platinum Taq polymerases, Tbr polymerase, Tfl polymerase, Pfu-turbo polymerase, Pyrobest polymerase, Pwo polymerase, KOD polymerase, Bst polymerase, Sac polymerase, Klenow fragment, polymerase with 3' to 5' exonuclease activity, and variants, modified products and derivatives thereof. In some cases, the polymerase is a single subunit polymerase. The polymerase can have high processivity, namely the capability of the polymerase to consecutively incorporate nucleotides into a nucleic acid template without releasing the nucleic acid template. In some cases, a polymerase is a polymerase modified to accept dideoxynucleotide triphosphates, such as for example, Taq polymerase having a 667Y mutation (see e.g., Tabor et al, PNAS, 1995, 92, 6339-6343, which is herein incorporated by reference in its entirety for all purposes). In some cases, a polymerase is a polymerase having a modified nucleotide binding, which may be useful for nucleic acid sequencing, with non-limiting examples that include ThermoSequenas polymerase (GE Life Sciences), AmpliTaq FS (ThermoFisher) polymerase and Sequencing Pol polymerase (Jena Bioscience). In some cases, the polymerase is genetically engineered to have discrimination against dideoxynucleotides, such as for example, Sequenase DNA polymerase (ThermoFisher).

The term "quencher," as used herein, generally refers to molecules that may be energy acceptors. Example quenchers, without limitation, include Black Hole Quencher Dyes (Biosearch Technologies) such as BH1-0, BHQ-1, BHQ-3, BHQ-10); QSY Dye fluorescent quenchers (from Molecular Probes/Invitrogen) such QSY7, QSY9, QSY21, QSY35, and other quenchers such as Dabcyl and Dabsyl; Cy5Q and Cy7Q and Dark Cyanine dyes (GE Healthcare). Examples of fluorophore donor molecules that can be used in conjunction with above quenchers include, without limitation, fluorophores such as Cy3B, Cy3, or Cy5; Dy-Quenchers (Dyomics), such as DYQ-660 and DYQ-661; and ATTO fluorescent quenchers (ATTO-TEC GmbH), such as ATTO 540Q, 580Q, 612Q.

The terms "about" and "approximately" shall generally mean an acceptable degree of error for the quantity measured given the nature or precision of the measurements. Typical, examples of degrees of error are within 20 percent (%), within 10%, or within 5% of a given value or range of values. Alternatively, and particularly in biological systems, the terms "about" and "approximately" may mean values that are within an order of magnitude, within 5-fold, or within 2-fold of a given value. Numerical quantities given herein are approximate unless stated otherwise, meaning that the term "about" or "approximately" can be inferred when not expressly stated.

Methods and Systems For Improved Sequencing With Single Frequency Detection

Methods and systems of the present disclosure may detect optical signals from nucleotides to determine sequencing reads at higher accuracy and efficiency. In some instances, optical signals may be detected during transient binding of the nucleotides.

In an aspect, a method for nucleic acid sequencing may comprise providing a substrate comprising a plurality of sets of nucleic acid molecules. A set of nucleic acid molecules may be a colony or array of nucleic acid molecules having sequence homology (or substantial sequence homology) to a nucleic acid template. The substrate may comprise distinct sets of nucleic acid molecules, each set having sequence homology (or substantial sequence homology) to a nucleic acid template. Between any two sets, the respective nucleic acid templates may be the same template or different templates. In some instances, a plurality of nucleic acid molecules having substantial sequence homology may comprise at least 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or higher percentage of identity between any two sequences in the plurality of nucleic acid molecules. In some instances, a plurality of nucleic acid molecules having substantial sequence homology may comprise at least 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or more nucleic acid molecules in the plurality having sequence homology.

A first reaction mixture may be introduced to the substrate, under conditions sufficient to permit transient binding of nucleotides in the reaction mixture to the nucleic acid molecules in the substrate.

In some instances, a nucleotide transiently bound to a nucleic acid molecule may dissociate from the nucleic acid molecule in a time period of at most 5 second, 4 seconds, 3 seconds, 2 second, 1 second, 0.5 seconds, 0.1 seconds, or less. Alternatively or in addition, the transiently-bound nucleotide may dissociate upon application of energy to the nucleotide, such as thermal energy or kinetic energy (e.g., as may be provided by washing), or upon action by an enzyme (e.g., a polymerizing enzyme replacing the transiently bound nucleotide with another nucleotide). Alternatively or in addition, the transiently-bound nucleotide may dissociate upon application of a stimulus (e.g., photo stimulus, thermal stimulus, chemical stimulus, enzymatic stimulus, etc.). The nucleotide may be configured such that upon action by a polymerizing enzyme (e.g., polymerase) on the nucleic acid molecule, the nucleotide is transiently bound. Such transiently-bound nucleotide may be replaced by another nucleotide that is configured for transient binding or, alternatively, a nucleotide that is configured for non-transient binding (e.g., permanent incorporation).

The first reaction mixture may comprise at least two different base types (e.g., A, U, G, C, etc.) of nucleotides. For example, the first reaction mixture may comprise two base types, three base types, or four base types. A nucleotide in the first reaction mixture may be terminated or unterminated. The nucleotide in the first reaction mixture may be configured to transiently bind to, but not incorporate into, a nucleic acid molecule (and/or polymerase or polymerase complex). A nucleotide in the first reaction mixture may be labeled or unlabeled. Alternatively or in addition, a nucleotide in the first reaction mixture may be configured to be detectable or undetectable. The first reaction mixture may comprise both labeled and unlabeled nucleotides of the same base type. For a given base type, there may be x fraction of labeled nucleotides and (1-x) fraction of unlabeled nucleotides, where x is a positive value less than 1. The ratio of x/(1-x) may vary between different base types in the reaction mixture. In some instances, x may be at least about 0.00001, 0.0001, 0.001, 0.01, 0.1, 0.2, 0.3, 0.4, 0.5 or higher. In some instances, x may be at most about 0.99999, 0.9999, 0.999, 0.99, 0.9, 0.8, 0.7, 0.6, 0.5, or lower. Alternatively, x may be 0 or 1. In such a case where x is 1, the ratio of x/(1-x) may be undefined, but the respective fractions of x and (1-x) may still be known. For example, the percentage of labeled nucleotides for a first base type (e.g., C) may be any percentage from 0% to 100%, the remainder being unlabeled nucleotides for the first base type (e.g., 72% labeled, 28% unlabeled for base type C). Each base type may have a different ratio of labeled to unlabeled nucleotides in the first reaction mixture. The ratio of labeled to unlabeled nucleotides for each base type may be known. Alternatively or in addition to, the relative order of the ratio of labeled to unlabeled nucleotides as to each base type may be known (e.g., it may be known that the ratio of labeled to unlabeled for A is greater than for C which is greater than for U which is greater than for G). In some instances, all labeled nucleotides in the first reaction mixture, regardless of base type, may be labeled by the same dye and detectable by a same frequency or substantially the same frequency. Alternatively or in addition, labeled nucleotides in the first reaction mixture may be labeled by different dyes and configured to be detectable by a same frequency or substantially the same frequency.

After transient binding of nucleotides from the first reaction mixture to the nucleic acid molecules on the substrate, optical signals from the plurality of sets of nucleic acid molecules may be detected. Optical signals emitted from a first set of nucleic acid molecules and a second set of nucleic acid molecules from the plurality of sets of nucleic acid molecules may have the same or substantially the same frequency (e.g., same or substantially same wavelength). In some instances, where different base types were transiently bound as between the first set and the second set, the optical signals emitted from the first set and the second set may have different and distinct intensities. The type of nucleotide(s) transiently bound to each set of nucleic acid molecules may be identified based at least in part on the intensities of the optical signals detected from each set and the known ratios (or relative order of ratios) of labeled to unlabeled nucleotides of each base type in the first reaction mixture, thereby sequencing the nucleic acid template of each set. Beneficially, such as where the reaction mixture comprises four base types, the next base in the sequence read of each set on the substrate may be determined with a single reaction mixture and single detection frequency.

In some instances, after detection, the transiently bound nucleotides may be washed or otherwise un-bound from the nucleic acid molecules on the substrate, such as by heating or other methods described elsewhere herein. A second reaction mixture may be introduced to the substrate, under conditions sufficient to permit non-transient binding of nucleotides in the second reaction mixture to the nucleic acid molecules in the substrate. Such non-transient binding may be incorporation of the nucleotide. The second reaction mixture may comprise at least two different base types of nucleotides. For example, the second reaction mixture may comprise two base types, three base types, or four base types. The nucleotides in the second reaction mixture may be terminated, such as to prevent subsequent chain elongation (or extension) after incorporation of the terminated nucleotide. That is, after introduction of the second reaction mixture, each nucleic acid molecule on the substrate may be extended by at most one terminated nucleotide. The nucleotides in the second reaction mixture may be reversibly terminated. In an example, a terminated nucleotide having a 3'-OH blocking group may be unterminated by removing the blocking group, and the polymerase reaction can re-initiate. After incorporation of one terminated nucleotide in each nucleic acid molecule of the substrate, the substrate may be washed and subject to conditions to reverse termination of the terminated nucleotides to allow for subsequent polymerase reactions.

Thereafter, a third reaction mixture may be introduced to the substrate, under conditions sufficient to permit transient binding of nucleotides in the third reaction mixture to the nucleic acid molecules in the substrate. The third reaction mixture may be the same reaction mixture as the first reaction mixture. Alternatively, the third reaction may be a different reaction mixture in which the composition of nucleotides is known as in the first reaction mixture. The method described above (e.g., transient binding, followed by detection, followed by reversing transient binding, followed by non-transient incorporation, etc.) may be repeated any number of times to determine the next base reads in each set (or colony) of nucleic acid molecules on the substrate.

The plurality of sets of nucleic acid molecules may be a product of clonal amplification from template nucleic acid molecules. Having many thousands of identical copies of a template in a defined area may ensure that the detected cumulative intensity of the optical signal can be distinguished from different distinct areas and background noise. Massive parallelization can be facilitated by the creation of many millions of individual sequencing (e.g., by ligation or by synthesis) reaction centers, each with its own clonal template. A sequencing platform can collect information from many millions of reaction centers simultaneously, thus sequencing many millions of nucleic acid molecules in parallel. Such sequencing assay can be referred to as massively parallel sequencing. Some examples of massive parallel sequencing providers include, for example, SOLiD®, Complete Genomics®, Illumina®, Qiagen®, Roche 454®, Ion Torrent®, Pacific Biosciences®, Oxford Nanopore Technologies®, and 10x Genomics®.

A template nucleic acid molecule may be single stranded or double stranded. The template nucleic acid molecule may be a polynucleotide. The length of the polynucleotide can vary. For example, the polynucleotide can be at least about 1, 10, 20, 30, 40, 50, 100, 200, 300, 400, 500, 600, 700, 800, 900, 1,000, 2,000, 3,000, 4,000, 5,000, 6,000, 7,000, 8,000, 9,000, 10,000, 50,000, 100,000, or more nucleotides in length. Alternatively or in addition to, the polynucleotide can be at most about 500,000, 400,000, 300,000, 200,000, 100,000, 50,000, 10,000, 9,000, 8,000, 7,000, 6,000, 5,000, 4,000, 3,000, 2,000, 1,000, 900, 800, 700, 600, 500, 400, 300, 200, 100, 50, 40, 30, 20, 10 or fewer nucleotides in length.

The template can be amplified to generate a clonal copy, clonal copies, or clonal populations which comprise template-homologous strands (called "template strands" or "reverse strands" herein) and/or template-complementary strands (called "primer strands" or "forward strands" herein). Each clonal copy exhibits homology to the original template molecule. A clonal population can refer to a colony. Within a clonal population, each clonal copy is amplified from the same template molecule. In some cases, clonality can be maintained in the resulting amplified nucleic acid populations by maintaining association between template strands and its primer strands, thereby effectively associating or "tethering" associated clonal progeny together and reducing the probability of cross-contamination between different clonal populations. A clonal population of substantially identical nucleic acids can have a spatially localized or discrete macroscopic appearance. A clonal population can resemble a distinct spot or colony. In some cases, one or more amplified nucleic acids in the clonal population can be attached to a support, such as the substrate described herein.

One or more nucleic acid molecules described herein may be immobilized on a support, such as prior to, during, and/or subsequent to amplification or sequencing. The support may be a material having a surface on or to which additional matter can be coupled to or appended. The support may be a solid support, such as a slide, a bead, a resin, a chip, an array, a matrix, a membrane, a nanopore, a substantially planar surface, a gel, or any substrate. The solid support may, for example, be a flat substrate (such as glass, plastic, silicon, etc.) or a bead (e.g., within a well of a substrate). The substrate may have surface properties, such as textures, patterns, microstructure coatings, surfactants, or any combination thereof to retain the bead at a given location (such as in a position to be in operative communication with a detector). When using a support that is substantially planar, the support may be physically separated into regions, for example, with trenches, grooves, wells, or chemical barriers (e.g., hydrophobic coatings, etc.). The support may be a flow cell or an open substrate. The support may comprise a biological support, a non-biological support, an organic support, an inorganic support, or any combination thereof. The support may have a plurality of independently addressable locations. The nucleic acid molecules may be immobilized to the support at a given independently addressable location of the plurality of independently addressable locations. Immobilization of each of the plurality of nucleic acid molecules to the support may be aided by the use of an adaptor. Immobilization on the support may be aided by an adaptor. In some instances, a nucleic acid molecule can be attached to a support using one or more phosphoramidite linkers.

An optical signal may be any signal that can be optically detected. In some cases, a reporter moiety that is coupled to a nucleotide can generate such a signal. Coupling may be covalent or non-covalent (e.g., via ionic interactions, Van der Waals forces, etc.). Where covalent coupling is implemented, the reporter moiety may be coupled to the nucleotide via a linker, with non-limiting examples that include aminopropargyl, aminoethoxypropargyl, polyethylene glycol, polypeptides, fatty acid chains, hydrocarbon chains and disulfide linkages. In some cases, the linker is cleavable, such as photocleavable (e.g., cleavable under ultra-violet light), chemically-cleavable (e.g., via a reducing agent, such as dithiothreitol (DTT), tris(2-carboxyethyl)phosphine (TCEP)) or enzymatically cleavable (e.g., via an esterase, lipase, peptidase or protease). In some cases, the linker may be non-cleavable. In some examples, the reporter moieties comprise molecular structures that, once attached (e.g., transiently or non-transiently bound) to a nucleic acid sequence, provide a distinct characteristic that is not inherent to those nucleic acid molecules. In some cases the reporter moieties may create unique optical characteristics. In some cases, the reporter moieties can be used as a single signal generating entity or may be one of a pair of reporter moieties such that one reporter moiety performs the role of an energy donor, and the other reporter moiety performs the role of an energy acceptor. Energy donors and/or energy acceptors can both be fluorophore molecules. Whether a fluorophore is a donor or an acceptor may be based on its excitation and emission spectra, and the fluorophore with which it is paired.

A reporter moiety can be detectable by the presence of or a change in, color, fluorescence, reflectance, chemiluminescence, light polarization, light scattering, precipitation, x-ray scattering, electron spin resonance, or the deposition of an electron-rich substrate for visualization by electron microscopy. A reporter moiety may be detectable by its optical properties. The detectable response may be the presence of or a change in fluorescence, such as intensity, excitation or emission wavelength distribution of fluorescence, fluorescence lifetime, fluorescence polarization, or a combination thereof. Where the reporter moiety is a fluorophore, the reporter moiety may be a pyrene, an anthracene, a naphthalene, an acridine, a stilbene, an indole or benzindole, an oxazole or benzoxazole, a thiazole or benzothiazole, a 4-amino-7-nitrobenz-2-oxa-1,3-diazole (NBD), a cyanine, a porphyrin, a salicylate, an anthranilate, an azulene, a perylene, a pyridine, a quinoline, a coumarin (including hydroxycoumarins and aminocoumarins and fluorinated and sulfonated derivatives thereof), a 4-bora-3a,4a-diaza-s-indacene (e.g., U.S. Pat. No. 4,774,339 to Haugland, et al. (1988); U.S. Pat. No. 5,187,288 to Kang, et al. (1993); U.S. Pat. No. 5,248,782 to Haugland, et al. (1993); U.S. Pat. No. 5,274,113 to Kang, et al. (1993); and U.S. Pat. No. 5,433,896 to Kang, et al. (1995), each of which is entirely incorporated herein by reference), a xanthene, an oxazine or a benzoxazine, a carbazine (U.S. Pat. No. 4,810,636 to Corey (1989), which is entirely incorporated herein by reference), or a phenalenone or benzphenalenone (U.S. Pat. No. 4,812,409 Babb et al. (1989), which is entirely incorporated herein by reference), or a lanthanide chelate. In some embodiments, where the reporter moiety is a fluorophore, the reporter moiety is a carbazine, an oxazine, a coumarin, a xanthene, a naphthalene, a phenalenone, or a 4-bora-3a,4a-diaza-s-indacene. Where the reporter moiety is a xanthene, the reporter moiety may optionally be a fluorescein, a rhodol (U.S. Pat. No. 5,227,487 to Haugland, et al. (1993), which is entirely incorporated herein by reference), or a rhodamine. As used herein, fluorescein includes benzo- or dibenzofluoresceins, seminaphthofluoresceins, naphthofluoresceins or seminaphthorhodafluors (U.S. Pat. No. 4,945,171 to Haugland, et al. (1990), incorporated by reference). As used herein, oxazines include resorufins, aminooxazineones and diaminooxazines. Other examples of fluorophores include: fluorescein (e.g., 6-carboxyfluorescein (6-FAM)), Texas Red, HEX, Cy3, Cy5, Cy5.5, Pacific Blue, 5-(and-6)-carboxytetramethylrhodamine (TAMRA), and Cy7.

Examples of energy donor/energy acceptor fluorophore pairs include, but are not limited to, cyan fluorescent protein (CFP) and yellow fluorescent protein (YFP); Cy3 and Cy5; fluorescein and tetramethylrhodamine; IAEDANS and fluorescein; EDANS and dabcyl; fluorescein and QSY 7 or QSY 9 dyes; Alex Fluor 350 and Alexa Fluor 488; Alexa Fluor 488 and Alexa Fluor 546, 555, 568, 594, or 647; Alexa Fluor 568 and Alexa Fluor 647; and Alexa Fluor 594 and Alexa Fluor 85.

In some instances, the observable signal may be a product of quenching. In some instances, reporter moieties may be nucleic acid intercalator dyes. Examples include, but are not limited to ethidium bromide, YOYO-1, SYBR Green, and EvaGreen. The nearfield interactions between energy donors and energy acceptors, between intercalators and energy donors, or between intercalators and energy acceptors can result in the generation of unique signals or a change in the signal amplitude. For example, such interactions can result in quenching (i.e., energy transfer from donor to acceptor that results in non-radiative energy decay) or Forster resonance energy transfer (FRET) (i.e., energy transfer from the donor to an acceptor that results in radiative energy decay). Other examples of reporter moieties include electrochemical labels, electrostatic labels, colorimetric labels and mass tags. Such labels may be used with the systems and methods disclosed herein.

A detector may be used to detect the optical signal. The detector may be a device that is capable of detecting a signal, including a signal indicative of the presence or absence of a transiently bound nucleotide. In some cases, the detector can include optical and/or electronic components that can detect signals. Optical detection methods include, but are not limited to, fluorimetry and UV-vis light absorbance. A detector may use other detection methods, such as spectroscopic detection, electrostatic detection, electrochemical detection, and the like. Spectroscopic detection methods include, but are not limited to, mass spectrometry, nuclear magnetic resonance (NMR) spectroscopy, and infrared spectroscopy. Electrostatic detection methods include, but are not limited to, gel based techniques, such as, for example, gel electrophoresis. Electrochemical detection methods include, but are not limited to, electrochemical detection of amplified product after high-performance liquid chromatography separation of the amplified products.

The conditions for allowing transient binding of nucleotides can include adjusting or selecting parameters, such as time, temperature, pH, buffers, reagents, ionic strength, multivalent cations, salts, co-factors, nucleotides, template DNA, primer DNA, enzymes (e.g., nucleic acid-dependent polymerase), amounts and/or ratios of the components in the reactions, any reaction conditions, and the like. For example, the methods may use any polymerase which selectively binds a complementary nucleotide but exhibits reduced nucleotide incorporation activity, non-incorporatble nucleotides, the reaction conditions described elsewhere herein, non-extendible polymerization initiation sites, or a combination thereof.

In some instances, the transient binding reactions may be performed at reduced or elevated temperature. For example, the reduced temperature may be from about 4 to about 25° Celsius (° C.) or lower, and the elevated temperature may be from about 25 to about 80° C. or higher. In some instances, the conditions may comprise maintaining a pH range from about 6 to about 7.5. Alternatively, pH may be less than about 6. Alternatively or in addition, pH may be greater than about 7.5. In some instances, the conditions may comprise conducting the reaction with increased ionic strength. In some instances, the conditions may comprise reducing contact time between the polymerase and the nucleotide.

In some instances, the conditions may comprise conducting the reaction with a reduction, omission, or chelation of any metal ion which permits nucleotide incorporation, such as magnesium, manganese, cobalt, strontium, or barium, to inhibit nucleotide incorporation. For example, chelating agents may be used to render the cations unavailable for the incorporation reaction. In an example, the transient-binding reactions may be conducted under conditions that use manganese ions, Phi29 or RB69 polymerase, and certain types of nucleotides (e.g., nucleotides having 3-7 phosphates linked at the terminal phosphate group to a fluorophore via an intervening linker moiety).

In some instances, the conditions may comprise contacting a polymerase-template nucleic acid molecule complex in the presence of any cations that can inhibit nucleotide incorporation. The reaction conditions can include a period IV cation, such as calcium, scandium, titanium, vanadium, chromium, iron, cobalt, nickel, copper, zinc, gallium, germanium, arsenic, and selenium. The reaction conditions can include other multivalent cations, including rhodium or strontium. The period IV cation compound can be $ZnCl_2$, $CuCCl_2$, $CoCCl_2$, $FeSO_4$, or $NiCl_2$. The multivalent cation (e.g. calcium) may be added prior to, during, or subsequent to contacting the polymerase with the nucleic acid molecule and polymerization initiation site and/or contacting the polymerase with the nucleotide in the reaction mixture. In some instances, the reaction conditions can include calcium from about 0.1 miliMolar (mM) to about 50 mM. Alternatively, the reactions conditions can include less than 0.1 mM or greater than 50 mM of calcium.

In some instances, the reaction conditions can include at least one type of exchange-inert cation which is complexed with a nucleotide, to permit transient binding of the nucleotide to the polymerase and inducing ternary complex formation (or stabilizing the ternary complex), but inhibiting incorporation of the bound nucleotide. The transiently-bound nucleotide can be a complementary or non-complementary nucleotide. During nucleotide polymerization events, the polymerase can be in an open conformation prior to binding a nucleotide. Upon binding the complementary nucleotide, the polymerase can change to a closed conformation (also known as the ternary complex). The ternary complex can include the polymerase (in a closed conformation) which is bound to the template nucleic acid molecule which is base-paired with the polymerization initiation site, and the nucleotide. The polymerase, in a closed conformation, can catalyze incorporation of the bound nucleotide. Some cation-nucleotide complexes (e.g., chromium-nucleotides) promote the formation and/or stability of the ternary complex. The transient binding reactions can include at least one type of cation which promotes the formation and/or the stability of the ternary complex. In some instances, the transient binding reactions can be conducted with a polymerase bound to a nucleic acid template molecule which is base-paired with a polymerization initiation site and a Cr(III).nucleotide complex (e.g., a complementary nucleotide) without $Mg^{2+}$ or $Mn^{2+}$. The Cr(III).nucleotide complex can induce the formation of a ternary complex. The Cr(III) .nucleotide complex can be a chromium monodentate, bidentate, or tridentate complex. The Cr(III).nucleotide complex can be an α-monodentate, or β-γ-bidentate nucleotide.

In some instances, a polymerase used in the methods described herein may be a wild-type or modified polymerase that is configured to bind nucleotides but inhibit incorporation activity. The modified polymerases can be mutant polymerases, or can be polymerases which are bound to a cofactor to inhibit nucleotide incorporation. The selection of the polymerase for use in the transient-binding methods can be based on the combination of the polymerase and nucleotides, and the reaction conditions, to be used for the transient-binding step. In some instances, polymerases can be modified by binding it to a chemical compound or an antibody to inhibit nucleotide incorporation. The polymerase may be configured to bind incorporatable and/or unincorporatable nucleotides. In some instances, the polymerase can be an RB69 (exo-), a Phi29 (exo-), or B103 (exo-) polymerase, or a Klenow fragment. In some instances, the polymerization initiation site can include a terminal 3'OH extendible end or a terminal 3' non-extendible end.

In some instances, the conditions may comprise using non-incorporatable or terminated nucleotides, such as the nucleotide analogs or nonstandard nucleotides or modified nucleotides described elsewhere herein.

As an alternative to optical signals and optical detection, other types of signals and detection may be employed. For example, signals indicative of changes in conductivity, charge, or impedance may be measured to identify incorporation (or transient binding). An intensity level associated with such signals may be used to identify different types of bases (e.g., a mixture of A's may provide a different conductivity level than a mixture of G's).

Reference will now be made to the figures. It will be appreciated that the figures and features therein are not necessarily drawn (or shaded) to scale.

FIG. 1 illustrates a method for sequencing to identify four different base types using a single frequency. A plurality of sets of nucleic acid molecules is provided on a substrate 102. The substrate may be a solid support described elsewhere herein. For example, the substrate may be a planar surface. A set of nucleic acid molecules in the plurality of sets may be a colony (or clonal population) or array of nucleic acid molecules having sequence homology (or substantial sequence homology) to a nucleic acid template. The plurality of sets may include a first set 104a of nucleic acid molecules having sequence homology to a first nucleic acid template, a second set 104b of nucleic acid molecules having sequence homology (or substantial sequence homology) to a second nucleic acid template, a third set 104c of nucleic acid molecules having sequence homology (or substantial sequence homology) to a third nucleic acid template, a fourth set 104d of nucleic acid molecules having sequence homology (or substantial sequence homology) to a fourth nucleic acid template, and a fifth set 104e of nucleic acid molecules having sequence homology (or substantial sequence homology) to a fifth nucleic acid template. Each set may have sequence homology to a different nucleic acid template. Alternatively two or more sets may have sequence homology to the same nucleic acid template. In this example, the next base read in the first nucleic acid template of the first set 104a may be A, the next base read in the second nucleic acid template of the second set 104b may be G, the next base read in the third nucleic acid template of the third set 104c may be C, the next base read in the fourth nucleic acid template of the fourth set 104d may be A, and the next base read in the fifth nucleic acid template of the fifth set 104e may be T. Such next base reads are unknown and to be determined by the subsequent operations.

A reaction mixture 108 may be introduced to the substrate 102, under conditions sufficient to allow transient binding of nucleotides in the reaction mixture 108 to nucleic acid molecules in the five sets 104a-104e on the substrate 102. The reaction mixture may comprise at least two different base types (e.g., A, U, G, C, etc.) of nucleotides. The reaction mixture may comprise both labeled and unlabeled nucleotides of the same base type. For a given base type (e.g., C), there may be x fraction of labeled nucleotides and (1-x) fraction of unlabeled nucleotides, where x is a positive value less than 1. The ratio of x/(1-x) may vary across different base types in the reaction mixture 108. In some instances, x may be at least about 0.00001, 0.0001, 0.001, 0.01, 0.1, 0.2, 0.3, 0.4, 0.5 or higher. In some instances, x may be at most about 0.99999, 0.9999, 0.999, 0.99, 0.9, 0.8, 0.7, 0.6, 0.5, or lower. Alternatively, x may be 0 or 1. In such a case where x is 1, the ratio of x/(1-x) may be undefined, but the respective fractions of x and (1-x) may still be known. In some instances (not illustrated in FIG. 1), the ratio of labeled to unlabeled nucleotides may be lowest for base type G. In the example, the reaction mixture comprises unlabeled (e.g., natural and unlabeled, modified and unlabeled) nucleotides of base type A, labeled nucleotides of base type U, both labeled and unlabeled nucleotides of base type C, and both labeled and unlabeled nucleotides of base type G. Each base type may have a different ratio of labeled to unlabeled nucleotides in the first reaction mixture. The ratio of labeled to unlabeled nucleotides for each base type may be known. For example, in the illustrated example, the composition of the reaction mixture 108 may be:

A: 100% unlabeled, 0% labeled
U: 0% unlabeled, 100% labeled
C: 80% unlabeled, 20% labeled
G: 96% unlabeled, 4% labeled Alternatively or in addition to, the relative order of the ratio of labeled to unlabeled nucleotides as to each base type may be known (e.g., it may be known that the ratio of labeled to unlabeled for U is greater than for C which is greater than for G which is greater than for A). In some instances, all labeled nucleotides in the reaction mixture 108, regardless of base type, may be labeled by the same dye and detectable by a same frequency or substantially the same frequency.

Alternatively or in addition, labeled nucleotides in the reaction mixture may be labeled by different dyes and configured to be detectable by a same frequency or substantially the same frequency.

After transient binding of nucleotides from the reaction mixture 108 to the nucleic acid molecules on the substrate 102, optical signals from the plurality of sets of nucleic acid molecules may be detected. The first set 104a and the fourth set 104d may not emit optical signals because the reaction mixture comprises 100% unlabeled base type A nucleotides. The second set 104b, third set 104c, and fifth set 104e may emit optical signals having (and/or excited by) the same or substantially the same frequency. Based on the composition of the reaction mixture 108, the respective cumulative optical signals from the second, third, and fifth sets may have different intensities. For example, the intensity of the optical signal detected from the fifth set 104e which transiently binds 100% labeled nucleotides (U*) may be the highest. The intensity of the optical signal detected from the third set 104c which transiently binds 20% labeled (C*) and 80% unlabeled (C) nucleotides may be lower than the fifth set but higher than the second set 104e which transiently binds 4% labeled (G) and 96% unlabeled (G*) nucleotides. In the above example, thus, based on the intensities of the detected signals, it may be determined that the highest intensity set has a base read of T, the next highest intensity has a base read of C, the next highest intensity has a base read of G, and the lowest intensity has a base read of A. That is, the type of nucleotides transiently bound to each set of nucleic acid molecules may be identified based at least in part on the intensities of the optical signals detected from each set and the known ratios (or relative order of ratios) of labeled to unlabeled nucleotides of each base type in the reaction mixture, thereby sequencing the nucleic acid template of each set. Beneficially, such as where the reaction mixture comprises four base types, the next base in the sequence read of each set on the substrate may be determined with a single reaction mixture and single detection frequency.

In some instances, after detection, the transiently bound nucleotides may be washed or otherwise un-bound from the nucleic acid molecules on the substrate, such as by heating or other methods of stimuli (e.g., enzymatic, chemical, light cleavage, etc.). A second reaction mixture may be introduced to the substrate, under conditions sufficient to permit non-transient binding (e.g., incorporation) of nucleotides in the second reaction mixture to the nucleic acid molecules in the substrate. The nucleotides in the second reaction mixture may be reversibly terminated, such as to initially prevent subsequent chain elongation (or extension) after incorporation of the terminated nucleotide. That is, after introduction of the second reaction mixture, each nucleic acid molecule on the substrate may be extended by at most one terminated nucleotide. After incorporation of one terminated nucleotide in each nucleic acid molecule of the substrate 102, the substrate may be washed and subject to conditions to reverse termination of the terminated nucleotides to allow for subsequent polymerase reactions.

Thereafter, a third reaction mixture may be introduced to the substrate 102, under conditions sufficient to permit transient binding of nucleotides in the third reaction mixture to the nucleic acid molecules in the substrate. The third reaction mixture may be the same reaction mixture as the first reaction mixture. Alternatively, the third reaction mixture may be a different reaction mixture in which the composition of nucleotides is known as in the first reaction mixture. The method described above (e.g., transient binding, followed by detection, followed by reversing transient binding, followed by non-transient incorporation, etc.) may be repeated any number of times to determine the next base reads in each set (or colony) of nucleic acid molecules on the substrate.

Figure 2:
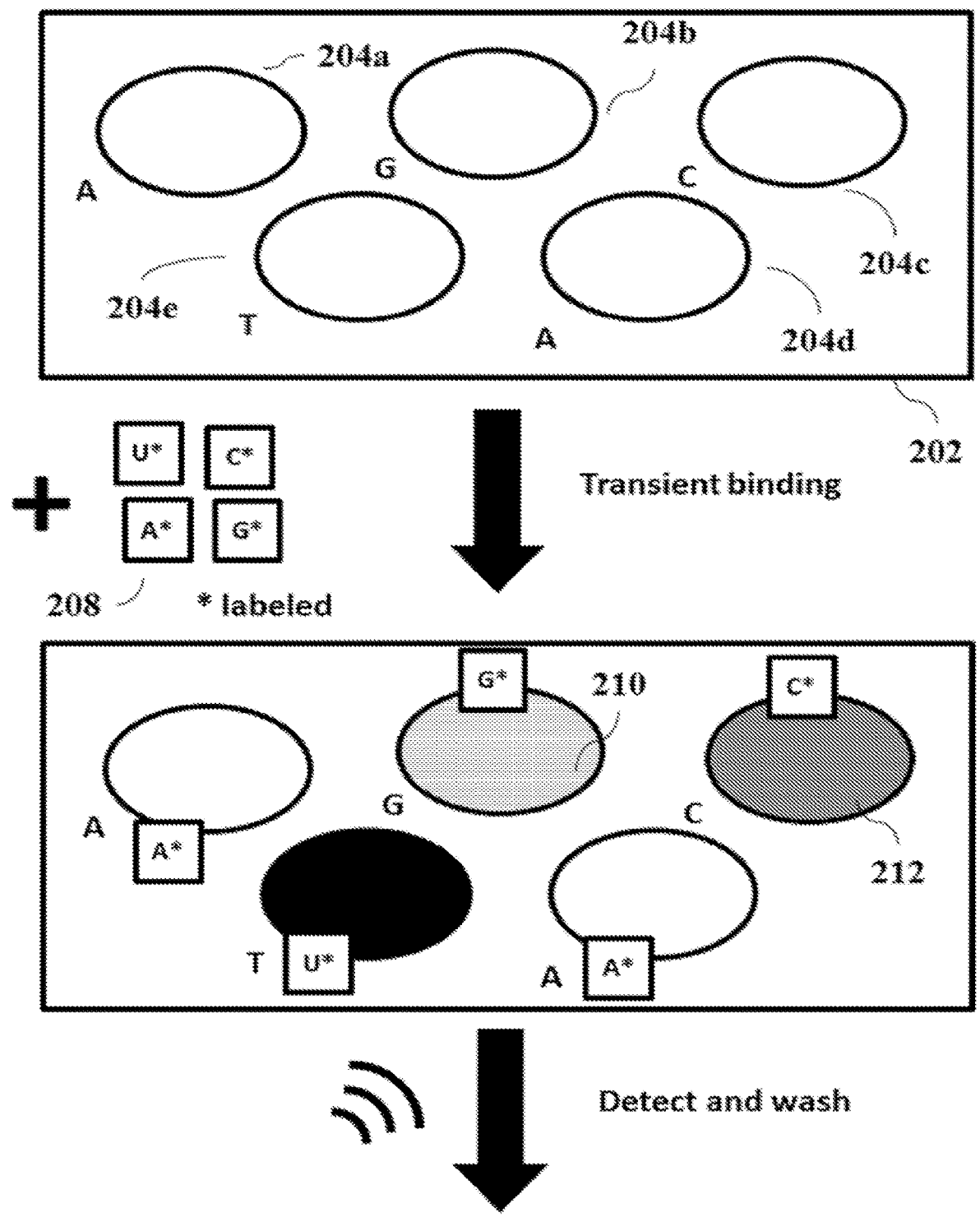
FIG. 2 illustrates another method for sequencing to identify four different base types using a single frequency.

FIG. 2 illustrates another method for sequencing to identify four different base types using a single frequency. A plurality of sets of nucleic acid molecules is provided on a substrate 202. The plurality of sets 204a-204e of nucleic acid molecules illustrated in FIG. 2 may correspond to the plurality of sets 104a-104e of nucleic acid molecules illustrated in FIG. 1.

A reaction mixture 208 may be introduced to the substrate 202, under conditions sufficient to allow transient binding of nucleotides in the reaction mixture 208 to nucleic acid molecules in the five sets 204a-204e on the substrate 202. The reaction mixture may comprise at least two different base types (e.g., A, U, G, C, etc.) of nucleotides. In the example, the reaction mixture comprises labeled nucleotides of base type A, labeled nucleotides of base type U, labeled nucleotides of base type C, and labeled nucleotides of base type G. The label on each base type may be detectable at the same frequency but emit an optical signal at a different intensity. For example, in the illustrated example, the composition of the reaction mixture 208 may be:

A: 100% labeled with a dye brightness normalized to 0.01 times the brightness of U U: 100% labeled with a dye brightness normalized to itself G: 100% labeled with a dye brightness normalized to 0.2 times the brightness of U C: 100% labeled with a dye brightness normalized to 0.6 times the brightness of U In some instances, the labeled nucleotides in the reaction mixture may be labeled by different dyes configured to be detectable by a same frequency or substantially the same frequency, but have different dye brightness.

After transient binding of nucleotides from the reaction mixture 208 to the nucleic acid molecules on the substrate 202, optical signals from the plurality of sets of nucleic acid molecules may be detected. The five sets 204a-204e may emit optical signals having (and/or excited by) the same or substantially the same frequency. Based on the dyes associated to each base type in the reaction mixture 208, the respective cumulative optical signals from the first, second, third, fourth, and fifth sets may have different intensities. For example, the intensity of the optical signal detected from the fifth set 204e transiently binding the labeled U* nucleotides may be higher than the third set 204c transiently binding the labeled C* nucleotides, which is higher than the second set 204b transiently binding the labeled G* nucleotides, which is higher than the first set 204a and the second set 204b, the first set and the second set having the same intensities from transiently binding the labeled A* nucleotides. In the above example, thus, based on the intensities of the detected signals, it may be determined that the highest intensity set has a base read of T, the next highest intensity has a base read of C, the next highest intensity has a base read of G, and the lowest intensity has a base read of A. That is, the type of nucleotides transiently bound to each set of nucleic acid molecules may be identified based at least in part on the intensities of the optical signals detected from each set and the known dye brightness of labeled nucleotides of each base type in the reaction mixture, thereby sequencing the nucleic acid template of each set. Beneficially, such as where the reaction mixture comprises four base types, the next base in the sequence read of each set on the substrate may be determined with a single reaction mixture and single detection frequency.

In some instances, after detection, the transiently bound nucleotides may be washed or otherwise un-bound from the nucleic acid molecules on the substrate, such as by heating or other methods described elsewhere herein. A second reaction mixture may be introduced to the substrate, under conditions sufficient to permit non-transient binding (e.g., incorporation) of nucleotides in the second reaction mixture to the nucleic acid molecules in the substrate. The nucleotides in the second reaction mixture may be reversibly terminated, such as to initially prevent subsequent chain elongation (or extension) after incorporation of the terminated nucleotide. That is, after introduction of the second reaction mixture, each nucleic acid molecule on the substrate may be extended by at most one terminated nucleotide. After incorporation of one terminated nucleotide in each nucleic acid molecule of the substrate 202, the substrate may be washed and subject to conditions to reverse termination of the terminated nucleotides to allow for subsequent polymerase reactions.

Thereafter, a third reaction mixture may be introduced to the substrate 202, under conditions sufficient to permit transient binding of nucleotides in the third reaction mixture to the nucleic acid molecules in the substrate. The third reaction mixture may be the same reaction mixture as the first reaction mixture. Alternatively, the third reaction may be a different reaction mixture in which the composition of nucleotides is known as in the first reaction mixture. The method described above (e.g., transient binding, followed by detection, followed by reversing transient binding, followed by non-transient incorporation, etc.) may be repeated any number of times to determine the next base reads in each set (or colony) of nucleic acid molecules on the substrate.

The methods illustrated in the FIGS. 1 and 2 may be applied to non-transiently binding sequencing by synthesis methods. For example, the first reaction mixture may be introduced to the substrate under conditions that allow nucleotides in the first reaction mixture to be non-transiently bound (e.g., non-transiently incorporated) to nucleic acid molecules on the substrate. The nucleotides in the first reaction mixture may be reversibly terminated, whether labeled or unlabeled, such that they are incorporated one base at a time, and detectable at a single frequency. The termination may be reversed, and the label cleaved, for example, before introducing another reaction mixture and repeating the above operation to sequence the nucleic acid templates. In some instances, a blocking group of the reversible terminator may comprise a reporter moiety (e.g., dye), such that upon removable of the blocking group, both the dye is removed and the termination is reversed. Alternatively, the reporter moiety may be attached to the nucleotide at a different location (e.g., the base) via an independent linker. In some instances, the linker for the blocking group and the linker for the dye may be the same type of linker and/or otherwise be cleavable via the same stimulus (e.g., cleaving agent). In other instances, they may be cleavable via different stimuli.

Computer Systems

Figure 3:
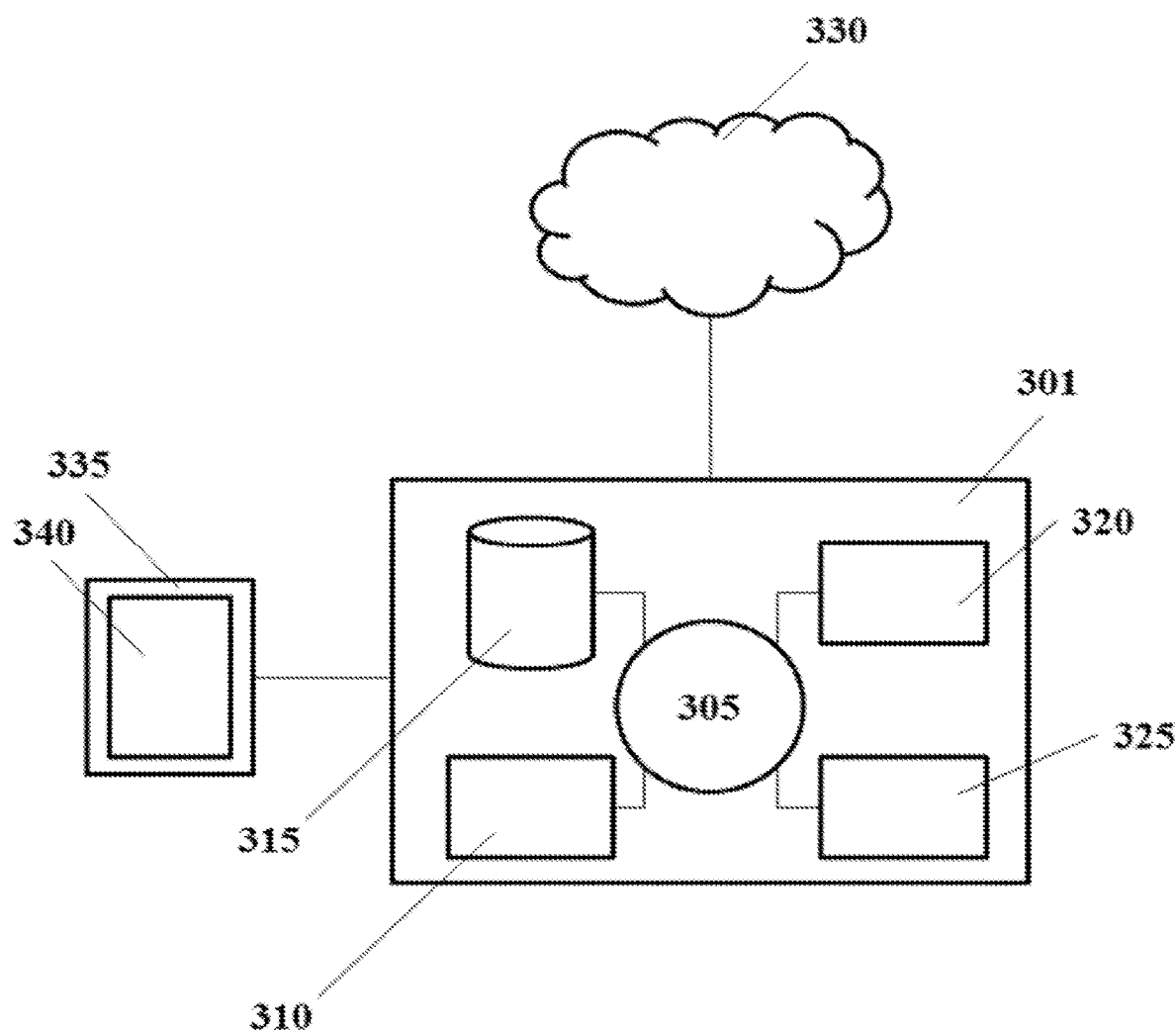
FIG. 3 shows a computer system that is programmed or otherwise configured to implement methods provided herein.

The present disclosure provides computer systems that are programmed to implement methods of the disclosure. FIG. 3 shows a computer system 301 that is programmed or otherwise configured to perform nucleic acid sequencing. The computer system 301 can determine sequence reads based at least in part on intensities of detected optical signals. The computer system 301 can regulate various aspects of the present disclosure, such as, for example, performing nucleic acid sequencing, sequence analysis, and regulating conditions of transient binding and non-transient binding (e.g., incorporation) of nucleotides. The computer system 301 can be an electronic device of a user or a computer system that is remotely located with respect to the electronic device. The electronic device can be a mobile electronic device.

The computer system 301 includes a central processing unit (CPU, also "processor" and "computer processor" herein) 305, which can be a single core or multi core processor, or a plurality of processors for parallel processing. The computer system 301 also includes memory or memory location 310 (e.g., random-access memory, read-only memory, flash memory), electronic storage unit 315 (e.g., hard disk), communication interface 320 (e.g., network adapter) for communicating with one or more other systems, and peripheral devices 325, such as cache, other memory, data storage and/or electronic display adapters. The memory 310, storage unit 315, interface 320 and peripheral devices 325 are in communication with the CPU 305 through a communication bus (solid lines), such as a motherboard. The storage unit 315 can be a data storage unit (or data repository) for storing data. The computer system 301 can be operatively coupled to a computer network ("network") 330 with the aid of the communication interface 320. The network 330 can be the Internet, an internet and/or extranet, or an intranet and/or extranet that is in communication with the Internet. The network 330 in some cases is a telecommunication and/or data network. The network 330 can include one or more computer servers, which can enable distributed computing, such as cloud computing. The network 330, in some cases with the aid of the computer system 301, can implement a peer-to-peer network, which may enable devices coupled to the computer system 301 to behave as a client or a server.

The CPU 305 can execute a sequence of machine-readable instructions, which can be embodied in a program or software. The instructions may be stored in a memory location, such as the memory 310. The instructions can be directed to the CPU 305, which can subsequently program or otherwise configure the CPU 305 to implement methods of the present disclosure. Examples of operations performed by the CPU 305 can include fetch, decode, execute, and writeback.

The CPU 305 can be part of a circuit, such as an integrated circuit. One or more other components of the system 301 can be included in the circuit. In some cases, the circuit is an application specific integrated circuit (ASIC).

The storage unit 315 can store files, such as drivers, libraries and saved programs. The storage unit 315 can store user data, e.g., user preferences and user programs. The computer system 301 in some cases can include one or more additional data storage units that are external to the computer system 301, such as located on a remote server that is in communication with the computer system 301 through an intranet or the Internet.

The computer system 301 can communicate with one or more remote computer systems through the network 330. For instance, the computer system 301 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 301 via the network 330.

Methods as described herein can be implemented by way of machine (e.g., computer processor) executable code stored on an electronic storage location of the computer system 301, such as, for example, on the memory 310 or electronic storage unit 315. The machine executable or machine readable code can be provided in the form of software. During use, the code can be executed by the processor 305. In some cases, the code can be retrieved from the storage unit 315 and stored on the memory 310 for ready access by the processor 305. In some situations, the electronic storage unit 315 can be precluded, and machine-executable instructions are stored on memory 310.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 301, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 301 can include or be in communication with an electronic display 335 that comprises a user interface (UI) 340 for providing, for example, results of nucleic acid sequence and optical signal detection (e.g., sequence reads, intensity maps, etc.). Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 305. The algorithm can, for example, implement methods and systems of the present disclosure, such as determine sequence reads based at least in part on intensities of detected optical signals.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for nucleic acid sequencing, comprising:
   (a) providing a substrate comprising at least a first set of nucleic acid molecules and a second set of nucleic acid molecules, wherein said first set of nucleic acid molecules has sequence homology to a first template, and wherein said second set of nucleic acid molecules has sequence homology to a second template, wherein said first template is different than said second template;
   (b) bringing said first set of nucleic acid molecules and said second set of nucleic acid molecules in contact with a reaction mixture comprising nucleotides of at least two different types comprising a guanine base type, under conditions sufficient to permit transient binding of at least a subset of said nucleotides to nucleic acid molecules of said first set of nucleic acid molecules and said second set of nucleic acid molecules, wherein a ratio of labeled to unlabeled nucleotides of said guanine base type is less than a respective ratio of labeled to unlabeled nucleotides of any other base type in said reaction mixture;

(c) detecting a first optical signal from said first set of nucleic acid molecules and a second optical signal from said second set of nucleic acid molecules, wherein said first optical signal and said second optical signal have a first frequency, and wherein said first optical signal and said second optical signal have different intensities; and (d) using said intensities of said first optical signal and said second optical signal to identify types of nucleotides of said at least said subset of said nucleotides transiently bound to said nucleic acid molecules of said first set of nucleic acid molecules and said second set of nucleic acid molecules, thereby sequencing said nucleic acid molecules of said first set of nucleic acid molecules and said second set of nucleic acid molecules.

2. The method of claim 1, wherein said nucleotides of at least two different types are configured to permit said transient binding.

3. The method of claim 1, wherein said conditions sufficient to permit said transient binding comprise presence of a metal cation.

4. The method of claim 3, wherein said metal cation is selected from the group consisting of calcium, scandium, titanium, vanadium, chromium, iron, cobalt, nickel, copper, zinc, gallium, germanium, arsenic, selenium, rhodium, and strontium.

5. The method of claim 1, further comprising, subsequent to (d), removing said at least said subset of said nucleotides transiently bound to said nucleic acid molecules of said first set of nucleic acid molecules and said second set of nucleic acid molecules.

6. The method of claim 5, further comprising heating said substrate to remove said at least said subset of said nucleotides transiently bound to said nucleic acid molecules of said first set of nucleic acid molecules and said second set of nucleic acid molecules.

7. The method of claim 5, further comprising bringing said first set of nucleic acid molecules and said second set of nucleic acid molecules in contact with an additional reaction mixture comprising nucleotides of at least two types, under conditions sufficient to permit non-transient binding of at least a subset of said nucleotides from said additional reaction mixture to said nucleic acid molecules of said first set of nucleic acid molecules and said second set of nucleic acid molecules.

8. The method of claim 7, further comprising repeating (b)-(d) with another reaction mixture comprising nucleotides of at least two different types, under conditions sufficient to permit transient binding of at least a subset of said nucleotides from said another reaction mixture to said nucleic acid molecules of said first set of nucleic acid molecules and said second set of nucleic acid molecules.

9. The method of claim 1, wherein said reaction mixture comprises a first set of nucleotides of a first type and a second set of nucleotides of a second type, wherein said first set of nucleotides of said first type and said second set of nucleotides of said second type comprise labeled nucleotides, and wherein said first set of nucleotides of said first type or said second set of nucleotides of said second type comprises unlabeled nucleotides.

10. The method of claim 9, wherein said first set of nucleotides of said first type and said second set of nucleotides of said second type comprise said unlabeled nucleotides.

11. The method of claim 9, wherein said labeled nucleotides of said first set of nucleotides of said first type and said labeled nucleotides of said second set of nucleotides of said second type are labeled by a same dye and excited by said first frequency.

12. The method of claim 9, wherein said labeled nucleotides of said first set of nucleotides of said first type and said labeled nucleotides of said second set of nucleotides of said second type are labeled by different dyes and excited by said first frequency.

13. The method of claim 1, wherein said reaction mixture comprises nucleotides of at least three different types.

14. The method of claim 13, wherein said reaction mixture comprises nucleotides of four different types.

15. The method of claim 1, wherein said reaction mixture comprises reversibly terminated nucleotides.

16. The method of claim 14, wherein said substrate comprises a third set of nucleic acid molecules and a fourth set of nucleic acid molecules, wherein said third set of nucleic acid molecules has sequence homology to a third template different than said first template and said second template, wherein said fourth set of nucleic acid molecules has sequence homology to a fourth template different than said first template, said second template, and said third template, wherein (c) further comprises detecting a third optical signal from said third set of nucleic acid molecules and a fourth optical signal from said fourth set of nucleic acid molecules, wherein said third optical signal and said fourth optical signal have a second frequency, and wherein said third optical signal and said fourth optical signal have different intensities.

17. The method of claim 16, wherein said third optical signal and said fourth optical signal have said first frequency of said first optical signal and said second optical signal.

18. The method of claim 17, wherein (b) comprises bringing said third set of nucleic acid molecules and said fourth set of nucleic acid molecules in contact with said reaction mixture comprising said nucleotides of four different types, under conditions sufficient to permit transient binding of at least a subset of said nucleotides of four different types to nucleic acid molecules of said third set of nucleic acid molecules and said fourth set of nucleic acid molecules, and wherein (d) further comprises using said intensities of said third optical signal and said fourth optical signal to identify types of nucleotides of said at least said subset of said nucleotides of four different types transiently bound to said nucleic acid molecules of said third set of nucleic acid molecules and said fourth set of nucleic acid molecules, thereby sequencing said nucleic acid molecules of said third set of nucleic acid molecules and said fourth set of nucleic acid molecules.

* * * * *